Figure 1:
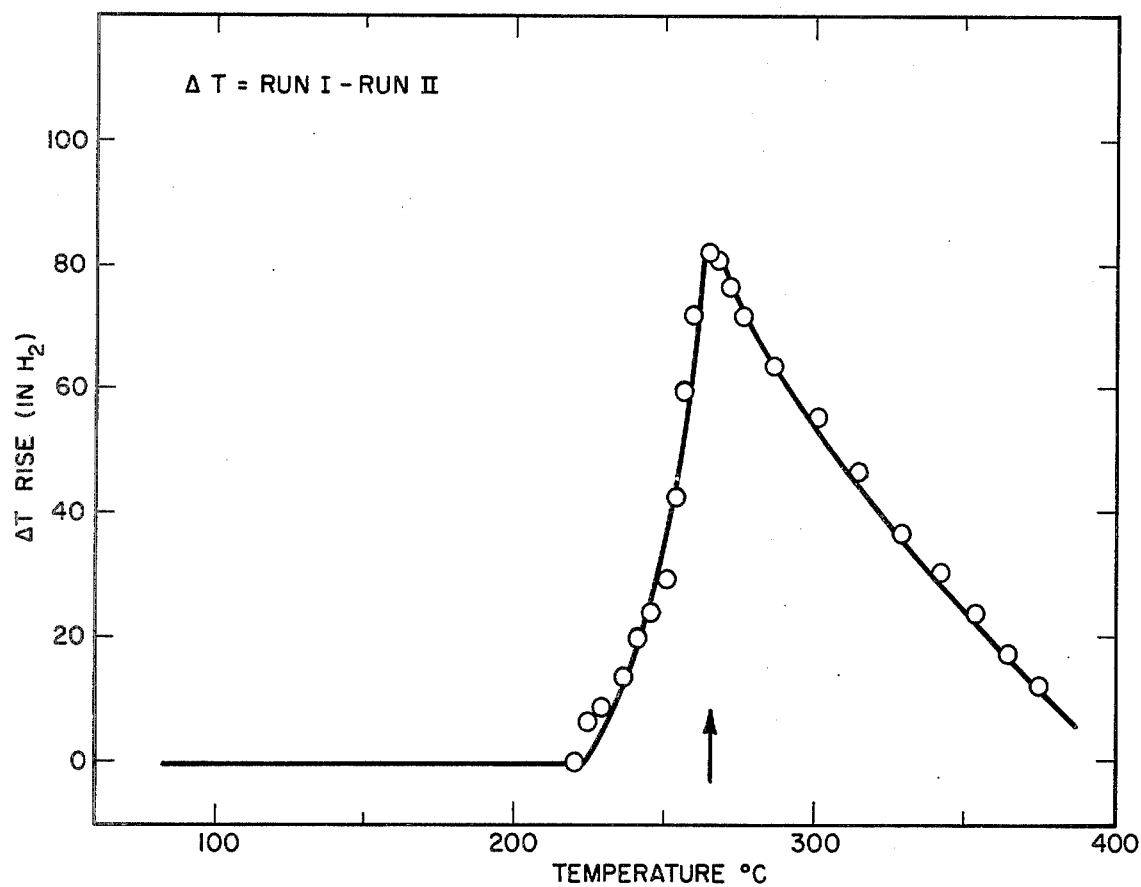

United States Patent [19]

Murrell et al.

[11] 4,160,745

[45] Jul. 10, 1979

[54] METHOD OF PREPARING HIGHLY ACTIVE NICKEL CATALYSTS AND CATALYSTS PREPARED BY SAID METHOD

[75] Inventors: Lawrence L. Murrell, Elizabeth; David J. C. Yates, West Millington, both of N.J.

[73] Assignee: Exxon Research & Engineering Co., Florham Park, N.J.

[21] Appl. No.: 856,262

[22] Filed: Dec. 1, 1977

[51] Int. Cl.$^2$ .................. B01J 21/04; B01J 21/08; B01J 21/12; B01J 23/74
[52] U.S. Cl. .................. 252/466 J; 252/447; 252/455 R; 252/455 Z; 252/472; 260/690; 585/270
[58] Field of Search .................. 252/459, 466 J, 472, 252/455 R, 455 Z, 447; 260/667

[56] References Cited

U.S. PATENT DOCUMENTS

| | | | |
|---|---|---|---|
| 1,268,692 | 6/1918 | Dewar et al. | 252/459 |
| 3,202,723 | 8/1965 | Thonon | 260/667 |
| 3,207,702 | 9/1965 | Flank et al. | 252/459 |
| 3,622,645 | 11/1971 | Carr et al. | 260/667 |
| 3,798,279 | 3/1974 | Cessou et al. | 260/667 |
| 3,987,099 | 10/1976 | Hockele et al. | 252/466 J |

*Primary Examiner*—W. J. Shine
*Attorney, Agent, or Firm*—Joseph J. Allocca

[57] ABSTRACT

The instant invention relates to a method for preparing high activity supported nickel catalysts. The method comprises the deposition of nickel nitrate on a carrier, typically an inert inorganic refractory oxide, by techniques known in the art followed by careful heating to a temperature of between 100° to 270° C., avoiding any excursions into temperatures beyond the stated maxima, in a flowing nonreactive gas atmosphere for a time sufficient to convert substantially all of the nickel nitrate into nickel oxide. When using an $H_2$ containing atmosphere the maximum temperature is 220° C. The supported nickel oxide resulting from the above procedure is then reduced to a supported nickel metal catalyst in a reducing atmosphere at a temperature ranging from about 230° C. to 400° C.

The instant invention also relates to a new class of supported nickel metal catalysts having a specific activity of at least twice the specific activities of prior art catalysts as determined for the hydrogenation of benzene. These catalysts comprise from 0.1 to 50 wt. % nickel on a support, preferably 0.5 to 20 wt. % nickel, most preferably about 17 wt. % nickel on a support, wherein the support is as defined above.

24 Claims, 1 Drawing Figure

METHOD OF PREPARING HIGHLY ACTIVE NICKEL CATALYSTS AND CATALYSTS PREPARED BY SAID METHOD

BRIEF DESCRIPTION OF THE INVENTION

The instant invention relates to a method for preparing high activity supported nickel catalysts. The method comprises the deposition of nickel nitrate on a carrier, typically an inert inorganic refractory oxide, preferably alumina, silica, silica-alumina, magnesia, titania, zirconia, kieselguhr, etc. and mixtures thereof, most preferably alumina, and silica-alumina, by techniques known in the art followed by careful heating to a temperature of between 100° to 270° C., preferably 150° to 230° C., most preferably 200° to 230° C., avoiding any excursions into temperatures beyond the stated maxima, in a flowing gas atmosphere, i.e. oxidizing atmosphere or reducing atmosphere of any gas which does not decompose at the temperature used and does not contain hydrogen, typically $O_2$, Air, $N_2$, argon, neon, helium, $CO_2$, CO, etc. and combinations thereof for a time sufficient to convert substantially all of the nickel nitrate into nickel oxide. When using an $H_2$ containing atmosphere the maximum temperature is 220° C. The preferred temperature range is 100°–220° C., most preferably 200°–220° C. The supported nickel oxide resulting from the above procedure is then reduced to a supported nickel metal catalyst in a reducing atmosphere at a temperature ranging from about 230° C. to 400° C., preferably 230° C. to 350° C., most preferably 230°–300° C.

The instant invention also relates to a new class of supported nickel metal catalysts having a specific activity of at least twice the specific activities of prior art catalysts as determined for the hydrogenation of benzene. These catalysts comprise from 0.1 to 50 wt.% nickel on a support, preferably 0.5 to 20 wt.% nickel, most preferably about 17 wt.% nickel on a support, wherein the support is as defined above.

PRIOR ART

Supported nickel catalysts are widely used in many industrial applications such as hydrogenation of unsaturated compounds to their paraffinic counterparts. Of great importance in such applications is the attainment of high activity and longevity on the part of the catalyst. Many, if not all, of the critical variables which determine the activity, longevity and selectivity of the catalyst are encountered during catalyst preparation and must be uniformly and repeatably controlled. Methods of metal salt deposition, drying calcining, reduction time, temperature, atmospheric composition, flow rate all enter into the problem of producing and reproducing a viable catalyst.

Calvin H. Bartholomew and Robert J. Farrauto in "Chemistry of Nickel-Alumina Catalysts" Journal of Catalysts 45 41–53 (1976) published a study of nickel-alumina catalysts. They indicated that a goal in the preparation of catalysts is to maximize the metal surface area of such catalysts. Typical preparation involves the deposition of a metal salt followed by decomposition of the metal salt to the oxide by calcination in air at 400°–500° C. followed by reduction in flowing hydrogen at 400°–500° C. to obtain well-dispersed metals. Increasing the reduction time or reduction temperature or nickel content generally increases the overall degree of nickel reduction. They state "Indeed ... more complete reduction to metallic nickel is possible, if the supported nickel salt is not calcined at all but is decomposed in hydrogen rather than air."

Various catalyst preparation techniques were employed by Bartholomew, et al. Typically, they involved the presence or absence of a calcination step followed by high temperature reduction. Surface areas and percentage nickel dispersion were determined. One example, however, involved no calcination but a slow rate of temperature rise under reducing conditions (a rate of $\sim 5°$ C./min with a 4-hour hold at 230° C.) with a probable final reduction temperature of 500° C. The material had a surface area of 14.6 $m^2/g$ with a % dispersion of 13.8. In later sections, Bartholomew, et al. indicate that the reduction temperature so as to maximize the extent of reduction to nickel metal is advantageously set at 500° C.

U.S. Pat. No. 3,798,279 to Cessou, et al. is directed to a process for hydrogenating aromatic hydrocarbons to naphthenic hydrocarbons and a catalyst for the process. The process utilizes two catalysts, the first is preferably Raney nickel or cobalt. The second catalyst is preferably a supported metal such as nickel or cobalt as an oxide. The specification stated that when supported the catalyst must be pretreated at temperatures of 150° to 300° C. in hydrogen and not at higher temperatures (320°–500° C.) to obtain the active catalyst. By way of example, the catalyst of the second reactor is prepared by impregnating 15% of nickel from nickel nitrate onto alumina pellets (250 $m^2/g$), drying and roasting at 300° C. for 6 hours (material 1). One portion of material 1 was then treated in pure $H_2$ for 15 hours at 250° C. It is reported that the resulting material is only nickel oxide. A separate portion of material 1 was treated with pure $H_2$ at 350° C. for 15 hours. It is reported that the resulting product is nickel in the metallic state.

Clearly, this patent does not teach the criticality of decomposing nickel nitrate on a support at temperatures less than 220° C. when using a hydrogen atmosphere (or the inadvisability of decomposing in hydrogen at temperatures over 220° due to runaway exothermicity).

U.S. Pat. No. 1,122,811 to Snelling teaches a method of making a catalyst from the metal formate. The patent goes on to say that "nickel, for example, when reduced from the oxide by hydrogen at 300° is in a different state and is more active than when reduced at 350°. For a maximum activity, the metal should be reduced at the lowest possible temperature and should be as nearly as possible, in an almost molecular state of fineness." This patent does not teach how to obtain the metal oxide, nor does it teach what low temperatures to use. This patent, coupled with U.S. Pat. No. 3,798,279 which shows no reductions at 250° C. teaches away from the process of the instant amplification wherein it is disclosed, and experimentally demonstrated, that temperatures as low as 230° C. can be utilized in the hydrogen reduction of supported nickel oxides which are themselves prepared by controlled low temperature decompsition of nickel nitrate.

U.S. Pat. No. 1,139,592 to Spieler deals with a method of preparing a catalyst from the nickel salt of an organic acid, such as nickel formate, by heating to a temperature of about 230° to 250° C. Clearly, this is neither a hydrogen reduction of nickel oxide nor a low temperature decomposition of nickel nitrate to nickel oxide.

U.S. Pat. No. 1,268,692 to Dewar, et al. is also involved with catalyst preparation. In one example, platinum chloride and nickel nitrate are poured into a boiling solution of caustic soda and formalin. The solution is precipitated, filtered and washed. The precipitate is reportedly reduced in hydrogen at 200° C. for 4 hours.

U.S. Pat. No. 2,151,329 to Page, et al. teaches the preparation of a nickel-alumina catalyst by adding a solution of nickel nitrate and aluminum nitrate to a solution of sodium carbonate to coprecipitate together nickel oxide and aluminum oxides and reducing the nickel oxide. The reduction is described as occurring in a carbon monoxide or hydrogen atmosphere at a temperature of about 250° C.

"Thermal Studies of Nickel, Cobalt, Iron and Copper Nitrates" by W. M. Keely and Harry W. Maynor, J. Chem. Eng. Data 8 297, 1963 presents a modern study of the decomposition characteristics of various nitrates, including nickel nitrate. This article states categorically that a temperature of approximately 400° C. is needed before complete decomposition to nickel oxide occurs. This article, in conjunction with U.S. Pat. No. 3,798,279 which states that no reduction of nickel oxide occurs at 250° C. in hydrogen clearly teaches away from the process and the superior compositions of the instant invention.

The instant invention relates to a new class of high activity supported nickel catalysts. These catalysts possess specific activities of at least 20 (as defined in the following section) for the hydrogenolysis of aromatics. The supports are typically an inert inorganic refractory oxide such as alumina, silica-alumina, silica, magnesia, titania, zirconia, zirconium-titanate, zeolites, etc., preferably alumina and silica-alumina, most preferably alumina. The support has a surface area ranging from 20 to 700 $m^2/g$, preferably 50 to 300 $m^2/g$, most preferably 150 to 250 $m^2/g$, as measured by nitrogen adsorption at 77° K. The metal loading of such new high activity supported nickel catalysts is in the range of 0.1 to 50 wt. %, preferably 0.5 to 20 wt. %, most preferably 17 wt. %.

The method useful for the preparation of the above recited high specific activity supported nickel catalyst involves the deposition by techniques known in the art, i.e., incipient wetness technique, precipitation or impregnation of nickel nitrate on to the inert inorganic support of choice selected from the group consisting of alumina, silica, silica-alumina, magnesia, titania, zirconia, zirconium titanate, zeolites, carbon, preferably alumina, silica, magnesia and silica-alumina, most preferably alumina. The nickel nitrate may be dissolved in any convenient solvent, the only proviso being that the solvent be inert with respect to the support chosen and easily removable. The support bearing the nickel nitrate may then be dried at from 50° to 120° C. if desired. Such a drying step is not essential.

The nickel nitrate-support combination is decomposed to nickel oxide-support by low temperature heating in an atmosphere at temperatures ranging from 100° to 270° C., preferably 150° to 230° C., most preferably 200° to 230° C., for a time sufficient to convert essentially all of the nickel nitrate on the support to nickel oxide. Alternatively, completion of this conversion step can be visually detected since the characteristic orange color of nitrogen oxide disappears once conversion is finished. This decomposition is performed in a gas atmosphere i.e. oxidizing or reducing atmosphere of any gas content provided it does not decompose at the temperature used and does not contain hydrogen. Preferably, the gas is selected from the group consisting of $O_2$, $N_2$, He, Argon, Neon, CO, $CO_2$, $H_2O$ and mixtures thereof at a flow rate of at least 1 cc/min/gram, preferably at least 10 cc/min/gram, most preferably at least 30 cc/min/gram. Such nickel nitrate group decomposition is of great value on a commercial scale as expensive high temperature calcinations are avoided. Also, nitrate group decomposition is required for nickel catalysts on a commercial scale in order to avoid the formation of large volumes of nitric acid during the hydrogen reduction of the catalyst.

When the decomposition is performed in a flowing hydrogen containing atmosphere, however, the maximum decomposition temperature is 220° C. The preferred temperature range is 100°-220° C., most preferably 200°-220° C. Excursions beyond this temperature may result in runaway exothermic reactions, serious damage to the catalyst and possibly explosion. The essential feature, however, is the low temperature decomposition below the stated maximum temperature.

The nickel oxide-support combination which results from the low temperature decomposition has been, unexpectedly, fround to be activated readily by a low temperature reduction. The reduction is performed in a reducing atmosphere, typically $H_2$, or hydrogen mixed with $N_2$, He, Ar, or with hydrogen containing reactive organic groups such as ethylene, propylene, etc., preferably $H_2$, at temperatures ranging from 230° C. to 400° C., preferably 230° C.-350° C., most preferably 230°-300° C.

By means of the carefully controlled low temperature decomposition of the nickel nitrate to nickel oxide described above, a number of significant advantages result. The nickel oxide on the support is air stable and can be easily transported to its ultimate destination for on-site reduction to nickel metal on the support. Because of the low temperature reduction which is practiced, catalyst generation, as a practical matter, can be practiced at the catalyst use site. Further, the catalyst which results is remarkably superior to prior art catalysts having the same surface areas and percentages of dispersion. This is because, most importantly, and unexpectedly, the specific activity of these new catalysts for hydrogenation is at least twice that of prior art catalysts and usually much higher, on the order of 5 to 25 times the specific activity of prior art catalysts (for a given support). On the average the specific activity is at least double the specific activity of catalysts prepared and used in the prior art. As a practical matter, and for the purposes of this application, in absolute terms this means the catalysts of the instant invention have a specific activity of at least 20 for the hydrogenation of benzene (as defined in the following section).

Experimental Conditions for the Examples

Benzene hydrogenation was used to assess the utility of a series of nickel catalysts, comparing prior art catalysts to those of the instant invention and prepared by the process revealed and claimed in the instant application. This reaction was chosen because one of the main applications of nickel as a catalytic metal is to remove unsaturated components (e.g. aromatics and olefins) from feedstocks by hydrogenating them to paraffinic compounds.

The benzene hydrogenation reaction is very exothermic and pains have been taken to remove this heat by two methods: use of a high hydrogen flow relative to the benzene flow, and by the use of a feed consisting of only 10% benzene. The other component used was hexane. As this is a paraffin, it will not react with hydrogen over the nickel catalyst, and is thus truly an inert diluent for the experimental conditions employed.

In all cases, a catalyst charge of 0.25 gm was used. After reduction the catalyst was cooled to 75° C. in hydrogen. The feed of 10% benzene in hexane was then passed over the catalyst at a rate such that the $H_2:C_6H_6$ volume ratio was 54:1.

Using this diluted feed and the high hydrogen to benzene ratio, it has been possible to obtain stable catalyst bed temperatures and reproducible catalytic data. In fact, using the above conditions, stable bed temperatures were easily maintained (at 75° C.) even for very active catalysts having greater then 90% benzene conversion. The advantage of the above procedure is that it allows the benzene hydrogenation activities (in % benzene conversion) to be compared directly for catalysts of greatly different activity.

A conventional down-flow stainless steel reactor 14" in length and 0.5" in diameter was employed for the catalyst testing. All the catalysts in the examples were crushed to 20-40 mesh, and diluted with 10 g of 10 mesh Mini-Media (Coors Porcelain Co.) porcelain beads. The catalyst bed was supported on a wire mesh screen which was in turn supported on an inverted thermocouple well positioned in the middle of the catalyst bed (the catalyst bed was 3 cm in length). A pre-heat section was provided by an additional 10 g of porcelain beads. With a 0.25 g catalyst charge (used in all examples except Example 5) convenient liquid feed rates of from 5 to 80 cc/hr of the 10 wt% benzene in hexane feed provided the range of conversions which established the order of the reaction in benzene for these conditions to be zero. In addition, the benzene hydrogenation conditions above were established to be free from mass transfer limitations using the methods described by Koros and Nowak (Chem. Engr. Sci., 22, 470 1967). Therefore, the percent benzene conversion is a direct measure of the catalytic activity of a given catalyst, and can therefore be employed to compare one catalyst activity to another. The temperature employed for all catalyst tests was 75° C. All the activity comparisons are for a liquid feed rate of 20 cc/hr of the 10 wt% benzene in hexane feed.

In summary, the following experimental conditions were used in the catalytic experiments:
Catalyst temperature: 75° C.
Feed: 10% benzene in hexane
Flow rate of benzene: 1.32 gm/hr
Flow rate of hydrogen: 20.4 liters/hr
Catalyst charge: 0.25 gms
Pressure: Atmospheric An important parameter which controls the activity of supported nickel catalysts, other physical factors (such as pore size) being equal, is the particle size of the nickel. For many systems this can be measured by X-ray diffraction line broadening. However, the more active a catalyst, the smaller the particle size of the nickel and active catalysts will often have particle sizes less than 50 A (i.e. $5 \times 10^{-7}$ cm). Unfortunately, the X-ray line broadening method is not applicable to particles smaller than 50 Å. For such particles, the only two methods commonly used are electron microscopy and chemisorption. The former, while direct, only measures a few micrograms of the catalyst in one photograph and hence has very severe sampling problems if the catalyst is at all nonuniform in nickel distribution. The chemisorption method depends on measuring the gas uptake of a gas which is adsorbed only on the nickel and not on the support. Such a gas is hydrogen; it is dissociatively adsorbed on clean nickel surfaces at room temperature, and is not physically adsorbed on the support (as the boiling point of $H_2$ is 21° K).

The whole chemisorption technique and its utility in correlating nickel particle size (and/or nickel surface area) with catalytic activity has been published in detail by one of the inventors of this application (D. J. C. Yates, W. F. Tayloer and J. H. Sinfelt, J. Amer. Chem. Soc., 86, 2996 (1964)).

FIG. 3 in that publication shows that a direct relation exists between nickel area (as $m^2$/gm of catalyst) and initial reaction rate for ethane catalytically converted into methane (as mmoles $C_2H_6$ converted per hour per gm catalyst). In other words, the rate of hydrogenolysis is proportional to the nickel surface area. This means that the specific activity of the catalyst, defined as the rate of ethane hydrogenolysis per unit area of nickel surface, remains essentially constant when the nickel surface area is varied over a threefold range.

Most commercial nickel catalysts utilize supports, generally oxides such as silica, alumina, silica alumina, etc. Early work by one of the inventors of this application (W. F. Taylor, D. J. C. Yates and J. H. Sinfelt, J. Phys. Chem., 68, 2962 (1964)) constituted one of the first detailed studies of the effect of the support on the catalytic activity of nickel in hydrogenolysis reactions.

The reaction studied was the hydrogenolysis of ethane, and it was found by using the hydrogen chemisorption technique described in the J. Amer. Chem. Soc. article that the specific activity of nickel varied considerably when the support was changed. For example, with 10% Ni on silica, the specific activity of ethane converted per hour per $m^2$ of Ni at 91° C. was found to be 15.5 (units: moles$\times 10^5$). For 10% Ni on alumina it was found to be 8.25 and for 10% Ni on silica-alumina it was found to be 0.293, all determined under identical experimental conditions (see Table I, J. Phys. Chem. 68, 2962 (1964)).

Evidently, then, for maximum practical effectiveness in nickel catalysis one needs to maximize two critical properties of the nickel: 1. The nickel surface area ($m^2$/gm catalyst); and 2. The specific activity (moles of reactant converted to the desired product per unit time per $m^2$ of nickel).

We have found that the hydrogenation of aromatics, such as benzene, is also very dependent on the nature of the support. For example, we have found that the specific activity of nickel on silica is considerably higher than that of nickel on alumina. Most unexpectedly, however, we have now found for the first time a method of varying the specific activity of nickel on alumina in such a way as to approach the specific activity of nickel on silica. More surprisingly, however, it has been discovered that the specific activity is dramatically increased while the nickel surface area has remained constant, i.e. the specific activity is increased without varying the surface area.

The specific activity values used in the application were obtained by dividing the benzene conversion (in %) under the standard catalytic conditions by the nickel surface area per gm of catalyst obtained by hydrogen chemisorption. The surface area determined by hydrogen chemisorption was determined for the supported nickel catalysts after reduction at 450° C. This was done for the sake of simplicity and uniformity. Hydrogenation of benzene, however, was determined after reductions at the temperatures stated in the examples. In order to obtain convenient numbers the percent benzene conversion measured experimentally was multiplied by a factor of ten before dividing by the nickel surface area. As discussed previously, the specific activity is the activity for a given surface area of nickel catalyst and is therefore a direct measure of the intrinsic activity of the catalyst, all test or comparison parameters being equal. A catalyst with a specific activity twice another catalyst would have twice the benzene conversion for a constant nickel surface area.

In summary, the activity comparisons and specific activities for the different catalysts in the following examples are for the benzene hydrogenation activity in terms of % benzene conversion and were obtained at a liquid feed rate of 20 cc/hr of the 10 wt. % benzene in hexane feed at 75° C.

EXAMPLE 1

A sample of a commercially available 10–12 wt. % nickel on alumina (T-310) was obtained from Girdler Chemical Inc., Louisville, Kentucky. The nickel surface area after reduction at 450° C. was found to be 4.7 square meters per gram of catalyst. This commercial catalyst is used for comparison with the improved catalysts of the current invention.

EXAMPLE 2

Another sample of the catalyst of Example 1 (Girdler T-310) was investigated for benzene hydrogenation after reduction of the catalyst at 450° C. in flowing hydrogen. The benzene conversion of this catalyst was 0.8% at our standard conditions described previously. The specific activity of this catalyst is 1.7. This example is for comparison with the improved catalysts of the current invention, and illustrates a specific catalyst activity representative of commercial nickel catalysts prepared by prior art methods.

EXAMPLE 3

A sample of an 8.8 wt% Ni on $Al_2O_3$ catalyst prepared on a commercial scale by aqueous incipient wetness impregnation, drying and calcining at 425° C. in air was obtained as an experimental catalyst. The nickel surface area (after reduction at 450° C.) of this catalyst was 3.7 square meters per gram of catalyst. This nickel surface area is not greatly different from the commercial Girdler catalyst of Example 1. This example serves to demonstrate that high temperature calcination conditions yield a nickel catalyst with a nickel area of about 2–5 square meters per gram of catalyst. This example is useful for comparison to the improved catalysts of the current invention.

EXAMPLE 4

The benzene conversion of the catalyst of Example 3 was obtained after reduction at 450° C. in flowing hydrogen and was found to be 2.2%. This catalyst has a specific activity of 5.9. This specific activity is 3.5 times higher than that of the catalyst of Example 2. This example is useful for comparison to the improved catalysts of the current invention.

EXAMPLE 5

A sample of high purity nickel powder described as Mond nickel powder was obtained from the International Nickel Co., New York. The nickel surface area of this powder as measured by hydrogen chemisorption was 0.65 square meters per gram after reduction in flowing hydrogen at 270° C. This low surface area is characteristic of metal powders and metal blacks and is a result of large metal aggregates always found in the absence of a support. As a result of the very low surface area of this catalyst, 2.5 g was charged to the reactor to obtain a reasonable conversion level. The benzene conversion of the catalyst was 2.8% after reduction in flowing hydrogen at 270° C. The specific activity of this catalyst is 43. This specific activity is 25 times greater than that of the catalyst of Example 2, and 7 times greater than that of the catalyst of Example 4. The specific activity of nickel powder is the intrinsic specific activity of nickel as there is no support present which might modify the catalytic properties of the nickel surface. This specific activity is useful for comparison to the improved supported catalysts of the current invention.

EXAMPLE 6

A nickel catalyst precursor was prepared as follows. Nickel nitrate hexahydrate, in aqueous solution, was added to 300 gms of a pure gamma alumina (of a purity sufficient to be used for reforming), the alumina being in the form of 1/16" extrudates, with a nitrogen surface area of 190 $m^2$/gm. The volume of the solution was such as to equal the pore volume of the alumina, hence the technique employed is essentially that of "incipient wetness". The quantity of nickel nitrate used was such that the catlyst would contain 17 wt% nickel metal after reduction. After addition of the nitrate, the sample was dried, in air, at 120° C. for 18 hours.

EXAMPLE 7

A 10 gm portion of the catalyst precursor described in Example 6 was calcined as in the prior art at 425° C. in a muffle furnace. The nickel surface area of this calcined catalyst as measured by hydrogen chemisorption, after a reduction in $H_2$ at 450° C. was 12 square meters per gram of catalyst. This catalyst has a nickel surface area much improved over that of the catalysts in Examples 1 and 3. However, this catalyst contains 17 wt% Ni while those in Examples 1 and 3 contain ca. 11 and 9 wt% Ni, respectively. Hence, the higher surface area is partly due to the increased nickel content.

The benzene hydrogenation activity of this 425° C. calcined catalyst after reduction at 450° C. in flowing hydrogen was 8%, giving a specific activity of 6.7. This specific activity is very close to the commercially calcined catalyst of Example 4. This specific activity is useful for comparison to the improved catalysts of the instant application.

EXAMPLE 8

A 5 gm portion of the catalyst precursor described in Example 6 was reduced as in the prior art in flowing hydrogen at 450° C., and the surface area as measured by hydrogen chemisorption was 30 square meters per gram of catalyst.

Another portion of the catalyst precursor described in Example 6 was charged to the hydrogenation unit and reduced at 450° C. The benzene conversion was found to be 47%. The specific activity of this catalyst with a surface area of 30 $m^2$/g of catalyst is 15.7. This example serves to demonstrate that calcination by the procedure of the prior art as in Example 7 decreases the nickel surface area and the specific activity compared to the catalyst of the present example. This specific activity of the catalyst of this example (8) is 2.3 times higher than the catalyst of Example 7. This example is also useful for comparison to the improved catalysts of the current invention.

EXAMPLE 9

A 100 gm aliquot of the catalyst precursor, prepared as described in detail in Example 6, was charged to a one inch diameter silica reactor, 36 inches long. The reactor was then placed in the middle of a furnace, controlled by a Data-Track Programmer Controller Model 5500/624A, made by Research Inc., Minneapolis. After purging out the reactor with high purity nitrogen, hydrogen was introduced in quantities sufficient to give a gas mixture containing 17% $H_2$ in $N_2$. The flow rate was 43 cc per minute per gram of material. The furnace was then heated at a linear rate of 1° C. per min. from 20° to 80° C. and then at 0.5° C./min. from 80° to 220° C. When the catalyst reached 220° C., this temperature was held constant for about 6 hours. This resulted in the essentially complete decomposition of the nickel nitrate into nickel oxide, as was shown by the absence of the evolution of the characteristically orange nitrogen oxides after this time.

We considered it possible that during this hydrogen decomposition of the nickel nitrate, some free nickel metal might have been produced. If this were so, the catalyst would become very exothermic on air addition. To determine the state of the catalyst after hydrogen decomposition, the following experiment was performed.

At the end of the 6 hour period at 220° C. in 17% $H_2$, the hydrogen flow was cut off while the catalyst was still at 220° and pure $N_2$ passed over the catalyst for 15 minutes. This purged the catalyst of any adsorbed hydrogen. The power was then cut to the furnace and the catalyst cooled to room temperature overnight in the flowing $N_2$. In the morning, 1% oxygen was added to the $N_2$ and no significant increase in temperature of the catalyst bed was measured. Again, no heat release was detected when the oxygen concentration was increased to 10%, nor on bringing air over the catalyst.

This demonstrates two very important points:
1. After a decomposition (in $H_2$) carried out by the method of the instant invention, the nickel is in the form of nickel oxide and not nickel metal.
2. From this follows the extremely important practical point that a nickel catalyst, after having the nitrate groups removed in $H_2$ by the procedure of the present invention, can be safely brought into the air without any danger of fire or explosion. It is, of course, well known in the art that nickel catalysts, in the reduced state, are highly pyrophoric and can easily ignite on exposure to air.

It is evident that one of the preferred embodiments of our instant invention is to perform the decomposition of the nickel nitrate in vessel A, which may be in a convenient manufacturing location, and then transship this material to the plant where the reactor (or vessel B) is located. After reduction to the metal in vessel B, the catalyst is ready for use.

EXAMPLE 10

A portion of the supported nickel oxide of Example 9 was charged to the surface area apparatus and reduced at 450° C. in flowing hydrogen. The surface area as measured by hydrogen chemisorption was 28 square meters per gram of catalyst. This nickel surface area is similar to that obtained for the catalyst of Example 8. However, the benzene hydrogenation conversion of this low temperature decomposed catalyst was 67% following a 270° C. reduction for 2 hours. The specific activity of this catalyst is 23.9. This unexpected result serves to demonstrate the major improvement in the specific activity by 50% of a decomposed catalyst (Ex. 10) compared to directly reducing the catalyst precursor (Ex. 8) at 450° C.

Furthermore, this example also demonstrates the improvement in the specific activity by a factor of 3.6, which may be obtained by a low temperature decomposition compared to a calcined catalyst, (Example 10 versus Example 7).

Note also the specific activity of the catalyst of this example, 23.9, is directionally increasing toward the specific activity of unsupported nickel powder, 43, Example 5. The specific activity of the catalyst of Example 10, prepared by low temperature heat treatment, is 14.1 times the specific activity of the commercial supported nickel or catalyst of Example 2. This large improvement in specific activity is totally unexpected and constitutes one of the primary gains in the activity of the catalysts of the current invention.

These results are summarized in Table 1.

TABLE I

| Catalyst Example No. | Decomposition Conditions | Nickel Surface Area $m^2/g$ (reduced at 450° C. in $H_2$) | % $C_6H_6$ Conversion (Cat reduced at stated temp. °C.) | | Specific Activity |
|---|---|---|---|---|---|
| 2 (commercial) | — | 4.7 | 0.8 | (450) | 1.7 |
| 4 (commercial) | 425° C. in air | 3.7 | 2.2 | (450) | 5.9 |
| 5 (nickel powder) | — | 0.65 (at 270° C.) | 2.8 | (270) | 43 |
| 7 | 425° C. in air | 12 | 8.0 | (450) | 6.7 |
| 8 | — | 30 | 47 | (450) | 15.7 |
| 10 | 220° C. in $H_2$ | 28 | 67 | (270) | 23.9 |
| 11 | 220° C. in $H_2$ | 28 | 25 | (450) | 8.9 |
| 12 (A) | 220° C. in $H_2$ | — | 70 | (270) | — |
| 12 (B) | 220° C. in $H_2$ | — | 36 | (450) | — |
| 14 | 220° C. in $H_2$ | 24.6 | 53 | (230) | 21.5 |
| 15 | 220° C. in 3% $O_2$ in $N_2$ | 24.1 | 64 | (230) | 26.6 |
| 16 | 220° C. air (20% $O_2$) | 26.0 | 65 | (230) | 25 |

EXAMPLE 11

Another portion (wt. 0.25 gms) of the decomposed catalysts of Example 9 was charged to the reactor and reduced for 2 hours at 450° C. The benzene conversion of this catalyst was 25%.

This example, when compared to Example 10, shows the importance of the temperature of reduction of nickel catalysts as regards their activity for benzene hydrogenation.

The nickel surface area of the catalysts used in Examples 10 and 11 are the same, as is seen from Table I. Therefore, the marked difference in the hydrogenation activity of these two catalysts is due to changes in their specific activities, and has no relation to nickel dispersion. In addition, it is evident, for the first time, that a low temperature of reduction has a beneficial effect on the specific activity of nickel catalysts.

EXAMPLE 12

Another 100 gm aliquot of the catalyst precursor prepared as described in Example 6 was decomposed exactly as for Example 9. The benzene hydrogenation activity of this low temperature treated catalyst after a 270° C. reduction in flowing hydrogen was 70%. (A) The benzene hydrogenation activity of another portion of this catalyst after reduction at 450° C. in flowing hydrogen was 36%. (B)

This example serves to demonstrate the reproducibility of the decomposition process described in Example 9 as shown by comparison of the above data with the results obtained in Examples 10 and 11. This example again demonstrates clearly the detrimental effect of the high temperatures of reduction of the hydrogenation activity of nickel catalysts supported on alumina.

EXAMPLE 13

Another large batch of nickel on alumina catalyst precursor was prepared in a fashion identical with that described in detail in Example 6. However, instead of a reforming grade of alumina, we used a cheaper grade of commercial gamma alumina obtained from Akzo Chemie, Ketjen Catalysts Division, Amsterdam, The Netherlands. It was in the form of 1/16" extrudates, and had a surface area by nitrogen adsorption of 250 m$^2$/gm.

EXAMPLE 14

A 100 gm aliquot of the catalyst precursor of Example 13 was decomposed by heat treatment in 17% hydrogen as described in Example 9. The benzene hydrogenation activity of this catalyst after reduction at 230° C. in flowing hydrogen for 18 hours was 53%. The nickel surface area determined by hydrogen chemisorption following reduction at 450° C. in flowing hydrogen was 24.6 square meters per gram of catalyst. The specific activity of this catalyst is 21.5. This example serves to demonstrate the importance of the low temperature (230° C.) reduction of the above catalyst. The activity of this catalyst is not greatly different from the catalyst prepared on a different alumina, (Example 10) reduced at 270° C.

The above 230° C. activation was surprising, as all prior art on conventional nickel catalyst teaches that temperatures of at least 400° C. have to be employed to activate the catalyst. Furthermore, the ability of our decomposition process to give catalysts capable of in situ reduction at 230° C. is of great practical importance, as in many commercial units 230° C. is the highest temperature available for reduction.

EXAMPLE 15

A 100 gm aliquot of the catalyst of Example 13 was decomposed by the procedure described in Example 9, (220° C.) the only difference being the use of 3% O$_2$ in N$_2$, rather than 17% H$_2$ in N$_2$. The benzene hydrogenation activity of this catalyst after reduction at 230° C. in flowing hydrogen for 18 hours was 64%. The nickel surface area determined by hydrogen chemisorption following reduction at 450° C. in flowing hydrogen was determined to be 24.1 square meters per gram of catalyst. The specific activity of this catalyst is 26.6.

This example serves to demonstrate the low temperature (230° C.) reduction of the above catalyst. The activity of this catalyst is not greatly different from the catalysts of Examples 10, 12, and 14. This further demonstrates that our decomposition procedure while effective in hydrogen (Example 14), is even more effective when an oxidizing atmosphere is employed (as in this example).

EXAMPLE 16

A 100 gm aliquot of the catalyst of Example 13 was decomposed by the procedure described in Example 9, the only difference being the use of air, rather than 17% H$_2$ in N$_2$. The benzene hydrogenation activity of this catalyst after reduction at 230° C. in flowing hydrogen for 18 hours was 65%. The nickel surface area determined by hydrogen chemisorption following reduction at 450° C. in flowing hydrogen was determined to be 26.0 square meters per gram of catalyst. The specific activity of this catalyst is 25.0. The activity of this catalyst is not greatly different from the catalysts of Examples 10, 12, 14 and 15. Also, the low temperature activation (230° C.) of this catalyst is surprising as noted in Example 14. Data from Examples 13, 14, 15 and 16 are summarized in Table I.

EXAMPLE 17

To show the thermochemistry involved in rapid heat up of nickel catalyst precursors (in the form of dried nickel nitrate on alumina) the following experiments were performed in varying gaseous atmospheres in a silica furnace heated at a constant rate of rise from ambient temperature to 450° C.

Twenty grams of the precursor defined in Example 6 were loaded into the silica glass reactor which has been described earlier in Example 9. Glass wool was packed on the inlet side of the catalyst to act as a preheat bed. This thermocouple is denoted as the catalyst thermocouple as it measures the catalyst temperature. Another thermocouple was attached to the outside of the glass reactor and connected to a Data-Track Programmer-Controller Model 5500/524A, made by Research Inc., Minneapolis, Minnesota. This thermocouple is called the programmer thermocouple. This programmer was driven by a linear program set to give a linear rate of rise of 6° C./min from room temperature to 450° C. This it achieves by varying the current supplied to the furnace so that the programmer thermocouple increases in temperature at the rate of 6° C./min. The catalyst thermocouple (chromel-alumel) was connected to a chart recorder set for 0–20 millivolts, with the paper driven at a rate of 6" per hour. If there are no endothermic or exothermic reactions taking place in the catalyst bed, then the temperature of the catalyst will keep in step with the programmer thermocouple, i.e. it will increase at a rate of 6° C./min from room temperature to 450° C.

The first experiment (I) was done with dry air passing over the catalyst bed at a rate of 1 liter/minute. A broad region of endothermicity was found to exist between 180° and 270° C., with the catalyst being about 40° C. cooler than the programmed temperature over this region.

The second experiment (II) was done with a fresh charge of 20 grams of the catalyst precursor of Example 6 in the reactor, using identical preheat beds. The only difference was that instead of air, a mixture of 20% $H_2$ and 80% $N_2$ was used with a total flow of 1 liter/minute. The plot of catalyst temperature versus time obtained on the recorder was identical with the earlier run until 47 minutes into the heating cycle (catalyst temperature of 220° C.). At that point the catalyst temperature in $H_2$ (Run II) became hotter than the corresponding catalyst temperature obtained for the flowing air atmosphere (Run I), so much so that from being endothermic (i.e. catalyst temperature cooler than furnace temperature) it became exothermic (catalyst hotter than furnace temperature).

In order to correctly compensate for the endothermicity of heating up in air, the net heating effect due to $H_2$ in Run II was obtained by superimposing the recorder trace of Run I on that of Run II and the portion of the run where the catalyst is hotter in Run II, due to the presence of the $H_2$, being shown in FIG. 1.

Referring to the figure, it will be seen that the two runs had the same catalyst temperature until 220° C. was reached. Above that temperature the catalyst in Run II then rapidly became much hotter until at the maximum the catalyst in $H_2$ (Run II) was 82° C. higher than the catalyst in Run I. Expressed in another way, at the maximum ΔT in FIG. 1, the catalyst in air was at 265° C. while the catalyst in 20% $H_2$ was at 347° C.

It should be noted that these really quite excessive temperature rises occurred from a base temperature of 265° C. with a total flow of 1 liter per minute with a catalyst bed of 20 grams. This is a flow of 100 $cm^3$/min/gm, which is a flow per unit mass of catalyst much higher than can often be realized in large scale (tonnage) catalyst preparation.

Evidently, if one wishes to use reducing atmospheres (i.e. $H_2$) in the practice of the instant invention, while a high flow rate per unit mass of catalyst is important, the main control criterion must be to keep the catalyst at a temperature close to (or just below) 220° C. to avoid severe exothermic temperature runaways. Such severe exothermic conditions will obviously cause severe operating difficulties in large-scale operation, and lead to the production of catalyst with inferior properties, e.g. low specific activities and low nickel areas.

EXAMPLE 18

A rapid air calcination (referred to as a "flash" calcination) was performed as follows. A 20 gm aliquot of the catalyst precursor described in Example 6 was charged to the silica reactor described in Example 9. Air was passed over the catalyst at 27 $cm^3$/min and the temperature increased at a linear rate of 5° C./min from 20° C. to 425° C. On reaching 425° C. the catalyst was held at this temperature for 2 hours. It was then rapidly cooled, in flowing air, to room temperature.

A portion of this catalyst was charged to the hydrogenation reactor and reduced at 450° C. for 2 hours. The benzene conversion produced by this catalyst under our standard conditions was 8%. The nickel surface area of this catalyst, after reduction in $H_2$ at 450° C. was 12 square meters per gm of catalyst. It thus has a specific activity of 5.8.

This example shows the inferior activity of a "flash" calcined nickel catalyst compared with the procedure of the present invention as illustrated in Examples 10 and 12. This "flash" calcination procedure is modeled after conditions which have been used in the prior art of nickel manufacture.

EXAMPLE 19

A 17 wt% Ni catalyst on silica extrudates (obtained) from Akzo Chemie, Ketjen Catalyst Division) was prepared in the same manner as the catalyst of Example 6. A portion of the catalyst was flash calcined in air as for Example 18, (425° C. 2 hr). A portion of this catalyst was charged to the hydrogenation reactor and reduced at 270° C. in flowing hydrogen for 2 hours. The benzene hydrogenation activity of this catalyst was 0.8%.

Another portion of the uncalcined catalyst was decomposed in 3% $O_2$ by a procedure identical to that used in Example 15. The benzene hydrogenation activity of this catalyst following a 270° C. reduction for 2 hours in flowing hydrogen was 10%. This example serves to demonstrate the marked improvement in the hydrogenation activity of a nickel catalyst on a silica support decomposed in 3% oxygen at low temperatures compared to a catalyst-flash calcined by the prior art procedure. This example further serves to demonstrate the inferior hydrogenation activity of a nickel on silica catalyst compared to a nickel on alumina catalyst of equal nickel loading. (Examples 10 and 12).

EXAMPLE 20

A 17 wt% Ni catalyst on silica-alumina (W. R. Grace & Co., Davison Chemical Division, Baltimore, Maryland) was prepared in the same manner as the catalyst of Example 6. A portion of the catalyst was "flash" calcined as for Example 18. A portion of the latter catalyst was charged to the hydrogenation reactor and reduced at 270° C. for 2 hours in flowing hydrogen. The benzene hydrogenation activity of this catalyst was 6%.

Another portion of the uncalcined catalyst was decomposed in 3% $O_2$ by a procedure identical to that used in Example 15. The benzene hydrogenation activity of this catalyst, following a 270° C. reduction for 2 hours in flowing hydrogen, was 20%. This example serves to demonstrate the marked improvement in the hydrogenation activity of a nickel catalyst on a silica-alumina support decomposed at low temperatures in 3% $O_2$ compared to a "flash" calcined catalyst. This example further serves to demonstrate the inferior hydrogenation activity of a nickel on silica-alumina catalyst compared to a nickel on alumina catalyst of equal nickel content, Examples 10 and 12.

What is claimed is:
1. A process for the preparation of a supported nickel catalyst comprising the following steps:
    (a) depositing nickel nitrate on an inert inorganic refractory oxide support or carbon;
    (b) decomposing the nickel nitrate on the support to nickel oxide at a temperature of from 100° to 270° C. in a flowing gaseous atmosphere which gaseous atmosphere is characterized as not decomposing at the temperature utilized and does not contain hydrogen, said nickel nitrate decomposition being conducted essentially to completion as indicated by the cessation of the evolution of nitrogen oxides;
    (c) reducing the nickel oxide on the support of step (b) to nickel metal on the support under a reducing atmosphere at a temperature of from 230° to 350° C.

2. The process of claim 1 wherein the support is selected from the group consisting of alumina, silica, silica-alumina, magnesia, zirconia, titania, zirconium titanate.

3. The process of claim 2 wherein the support is alumina.

4. The process of claim 1 wherein the nickel nitrate is deposited on the support from solution.

5. The process of claim 4 wherein the nickel nitrate solution is aqueous.

6. The process of claim 1 wherein the decomposition temperature of step (b) ranges from 150° to 230° C.

7. The process of claim 1 wherein the decomposition temperature of step (b) ranges from 200° to 230° C.

8. The process of claim 1 wherein the reducing atmosphere of step (c) is a hydrogen containing atmosphere.

9. A supported nickel catalyst prepared by the process of the following steps:
(a) depositing nickel nitrate on an inert inorganic refractory oxide support or carbon;
(b) decomposing the nickel nitrate on the support to nickel oxide at a temperature of from 100° to 220° C. in a flowing hydrogen containing atmosphere, said nickel nitrate decomposition being conducted essentially to completion as indicated by the cessation of the evolution of nitrogen oxides; and
(c) reducing the nickel oxide on the support from step (b) to nickel metal on the support under a reducing atmosphere at a temperature of from 230° to 400° C.

10. The product prepared by the process of claim 9 wherein the nickel nitrate is deposited on the support from solution.

11. The product prepared by the process of claim 10 wherein the nickel nitrate solution is aqueous.

12. The product prepared by the process of claim 9 wherein the supports are selected from the group consisting of alumina, silica, silica-alumina, magnesia, zirconia, titania, zirconium titanate, zeolites and mixtures thereof.

13. The product prepared by the process of claim 12 wherein the support is alumina.

14. The product prepared by the process of claim 9 wherein the decomposition temperature of step (b) ranges from 200° to 220° C.

15. The product prepared by the process of claim 13 wherein the alumina has a surface area of from 20 to 700 $m^2/g$ determined by nitrogen adsorption at 77° K.

16. The product prepared by the process of claim 9 wherein the reducing atmosphere of step (c) is hydrogen.

17. The product prepared by the process of claim 9 wherein the temperture of reduction in step (c) is 230° to 350° C.

18. The product prepared by the process of claim 16 wherein the temperature of reduction of step (c) is 230°–300° C.

19. The process of claim 1 wherein the temperature of reduction of step (c) is 230°–300° C.

20. The process of claim 1 wherein the nickel metal loading of the catalyst ranges from 0.1–50 wt. %.

21. The product prepared by the process of claim 16 wherein the nickel metal loading of the catalyst ranges from 0.1–50 wt. %.

22. The process of claim 1 wherein the flow rate during decomposition step (b) is at least 10 cc/min/gram.

23. The product prepared by the process of claim 9 wherein the flow rate during decomposition step (b) is at least 10 cc/min/gram.

24. The product prepared by the process of claim 9 wherein the hydrogen containing atmosphere of step (b) is 17% $H_2$ in nitrogen.

* * * * *